United States Patent
Kim et al.

(10) Patent No.: US 10,625,077 B2
(45) Date of Patent: Apr. 21, 2020

(54) PORTABLE BODY SLIMMER TO STIMULATE CORE MUSCLE WITH RUSSIAN CURRENT

(71) Applicant: Med Sapiens Co., LTD, Seongnam-si, Gyeonggi-do (KR)

(72) Inventors: Hee soo Kim, Hanam-si (KR); Seung-won Seo, Gunpo-si (KR)

(73) Assignee: Med Sapiens Co., LTD, Seongnam-si, Gyeonggi-do (KR)

( * ) Notice: Subject to any disclaimer, the term of this patent is extended or adjusted under 35 U.S.C. 154(b) by 182 days.

(21) Appl. No.: 15/853,991

(22) Filed: Dec. 26, 2017

(65) Prior Publication Data

US 2019/0192853 A1    Jun. 27, 2019

(51) Int. Cl.
     *A61N 1/36*      (2006.01)
     *A61N 1/04*      (2006.01)
     *A61N 1/08*      (2006.01)

(52) U.S. Cl.
     CPC ....... *A61N 1/36034* (2017.08); *A61N 1/0452* (2013.01); *A61N 1/0468* (2013.01); *A61N 1/0476* (2013.01); *A61N 1/0484* (2013.01); *A61N 1/0492* (2013.01); *A61N 1/08* (2013.01); *A61N 1/36014* (2013.01); *A61N 1/36021* (2013.01); *A61N 1/36071* (2013.01); *A61N 1/36125* (2013.01)

(58) Field of Classification Search
     CPC .............. A61N 1/36034; A61N 1/0468; A61N 1/0484; A61N 1/08; A61N 1/36021; A61N 1/36071; A61N 1/36125; A61N 1/0456; A61N 1/0452; A61N 1/0476
     See application file for complete search history.

(56) References Cited

U.S. PATENT DOCUMENTS

2018/0304074 A1* 10/2018 Matsushita .......... A61N 1/3603

FOREIGN PATENT DOCUMENTS

| CN | 106964063 A | 7/2017 |
|---|---|---|
| JP | 2011-212431 A | 10/2011 |
| JP | 2016-202796 A | 12/2016 |

* cited by examiner

*Primary Examiner* — Paula J Stice
(74) *Attorney, Agent, or Firm* — Revolution IP, PLLC

(57) ABSTRACT

Disclosed herein is a drive device of an electrode channel for strengthening core muscles of an abdominal region, which can improve circulation of body fluid in a body cavity of the abdominal region and activate muscle membrane tissues inside/outside the abdominal cavity. The drive device includes a wearable instrument worn by a user over an abdominal region, a plurality of electrode channels formed by an electrode pair of a positive-terminal strip and a negative-terminal strip provided on the wearable instrument and contacting a body of the user, and a frequency supply unit for generating and selectively applying Russian current having a middle frequency and interference-wave current between the positive-terminal strip and the negative-terminal strip. Control is performed such that Russian current and interference-wave current are selectively applied to a positive-terminal strip of one of the plurality of electrode channels and a negative-terminal strip of another electrode channel.

9 Claims, 13 Drawing Sheets

PORTABLE BODY SLIMMER TO STIMULATE CORE MUSCLE WITH RUSSIAN CURRENT

BACKGROUND OF THE INVENTION

Field of the Invention

The present invention relates to a drive device of an electrode channel for strengthening core muscles of an abdominal region, and more particularly, to a drive device of an electrode channel for strengthening core muscles of an abdominal region, which is capable of improving circulation of body fluid in a body cavity of the abdominal region and activating muscle membrane tissues inside or outside an abdominal cavity.

Discussion of the Related Art

Generally, abdominal obesity means that body fat is excessively accumulated in an abdominal region and is caused by bad dietary habits, insufficient exercise, etc. Body fat accumulated in the abdominal region may increase risk of metabolic diseases such as hyperlipidemia and diabetes or cardiovascular disorders such as stroke and ischemic heart disease.

In addition, the core muscle located near the abdominal region supports the backbone, which is the center of the human body, and the pelvis of a person to prevent the backbone and the pelvis from being shaken. When the core muscle is weakened, since stability of the central region of the body is decreased, it is easy to cause imbalance such as scoliosis and slipped disk.

The core muscle supports the central region of the human body and plays an important role in maintenance of a posture. The core muscle includes transversus abdominis surrounding the abdominal region, multifidus muscles located at both sides of the backbone, the diaphragm taking part in breathing and serving to form an abdominal cavity and a thoracic cavity, and pelvic floor muscle surrounding the anus and genitals located at the bottom of the pelvis.

Examples of a method of treating abdominal obesity include a method of performing surgery or treatment or a method of strengthening muscles near an abdominal region through exercise. Removal of fat through surgery may damage the human body and cause serious side effects and thus is not preferred. Removal of fat through exercise is not achieved in a short period of time and requires steady efforts.

An electrostimulation device is responsible for applying electrostimulation to an abdominal region to break down fat and simulate abdominal muscles to strengthen muscles. If a user utilizes this device while exercising, abdominal obesity can be treated.

In a conventional low-frequency stimulator for muscle exercise, a winged pad extends around a central pad and a conductive electrode is attached to the winged pad. The adhesion properties of the electrode to the human body can be improved using an electrode protection film and low-frequency current can be stably delivered to the abdominal muscles.

However, portions, to which electrostimulation is applied by the winged pad, are restricted to the vicinity of the navel of the human body. In addition, since the frequency used for treatment is low and thus is delivered only to the outer layer of the skin, electrostimulation is only applied to the rectus abdominis, and is not applied to core muscles.

FIG. 1 shows the arrangement of general core muscles of the human body.

Referring to FIG. 1, the core muscles include the diaphragm, the transversus abdominis, multifidus muscle and pelvic floor muscle. The diaphragm serves to form an abdominal cavity and a thoracic cavity and lends stability upon breathing, thereby taking charge of 70% of breathing. The transversus abdominis serves to maintain the posture of the human body, and is located at the innermost side of the abdominal muscles to surround the central portion of the human body, thereby protecting most organs.

The multifidus muscle serves to guarantee orthostatism, and the pelvic floor muscle serves to support organs from below and is an important muscle for stabilization of the pelvis and movement of urine and feces.

When the core muscle is weakened, metabolism is lowered, and circulatory disturbances occur, thereby accumulating fat in an abdominal region. Accordingly, when the core muscle is strengthened, abdominal obesity can be prevented. Even when abdominal fat is removed, if a process of stimulating and strengthening core muscles is performed, it is possible to improve fat removal effects.

Among the core muscles, the transversus abdominis has a three-dimensional largest area and is disposed to be connected to the diaphragm, the multifidus muscle and the pelvic floor muscle, as shown in FIG. 1. In addition, the transversus abdominis is closely linked to abdominal obesity.

However, the abdominal muscle electrostimulation devices of the above-described document and the prior art focus on stimulation of the rectus abdominis and cannot uniformly stimulate the transversus abdominis although some stimulation is delivered to the transversus abdominis. In addition, the electrostimulation devices of the prior art are configured to apply pulses to an abdominal region in a vertical direction in order to stimulate the rectus abdominis having vertical stripes. However, since the transversus abdominis has horizontal stripes, it is difficult to efficiently stimulate the transversus abdominis using such vertical pulses.

SUMMARY OF THE INVENTION

Accordingly, the present invention is directed to a drive device of an electrode channel for strengthening core muscles of an abdominal region that substantially obviates one or more problems due to limitations and disadvantages of the related art.

An object of the present invention is to provide a drive device of an electrode channel for strengthening core muscles of an abdominal region, which is capable of stimulating internal organs and visceral fat to improve circulation ability of body fluid in a body cavity of the abdominal region and to activate muscle membrane tissues while strengthening core muscles and increasing effects of removing abdominal fat by applying Russian current or interference-wave current from positive-terminal strips to negative-terminal strips of different electrode channels in the positive-terminal strips and the negative-terminal strips configuring a plurality of electrode channels.

Additional advantages, objects, and features of the invention will be set forth in part in the description which follows and in part will become apparent to those having ordinary skill in the art upon examination of the following or may be learned from practice of the invention. The objectives and other advantages of the invention may be realized and attained by the structure particularly pointed out in the written description and claims hereof as well as the appended drawings.

To achieve these objects and other advantages and in accordance with the purpose of the invention, as embodied and broadly described herein, a drive device of electrode channels for strengthening core muscles of an abdominal region includes a wearable instrument worn by a user over an abdominal region, a plurality of electrode channels formed by an electrode pair of a positive-terminal strip and a negative-terminal strip provided on the wearable instrument and contacting a body of the user, and a frequency supply unit for generating and selectively applying Russian current having a middle frequency and interference-wave current between the positive-terminal strip and the negative-terminal strip. Control is performed such that Russian current and interference-wave current are selectively applied to a positive-terminal strip of one of the plurality of electrode channels and a negative-terminal strip of another electrode channel.

It is to be understood that both the foregoing general description and the following detailed description of the present invention are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this application, illustrate embodiment(s) of the invention and together with the description serve to explain the principle of the invention. In the drawings.

DETAILED DESCRIPTION OF THE INVENTION

Figure 1:
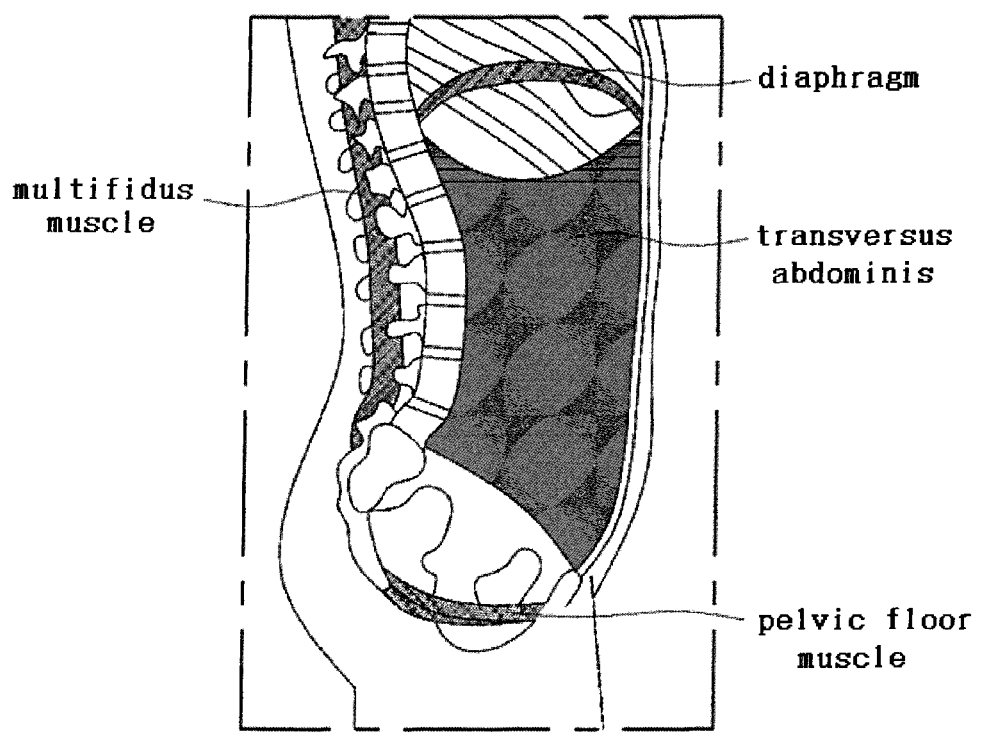
FIG. 1 shows the arrangement of general core muscles of the human body.

Reference will now be made in detail to the preferred embodiments of the present invention, examples of which are illustrated in the accompanying drawings. However, in the below description and the accompanying drawings, well-known structures and devices are omitted in order to avoid obscuring the concepts of the present invention. The same reference numbers will be used throughout the drawings to refer to the same or like parts.

The terms or words used in this specification and claims should not be interpreted to be limited to generally used terms, such as terms defined in a dictionary, and should be interpreted to coincide with the technical spirit of the present invention based on the principle that inventors can appropriately define the concepts of the terms in order to explain their inventions as best possible. Accordingly, the embodiments of the present invention and the configurations shown in the drawings are merely exemplary, do not represent all the technical spirit of the present invention and thus may be replaced by any equivalents and modifications.

Figure 2:
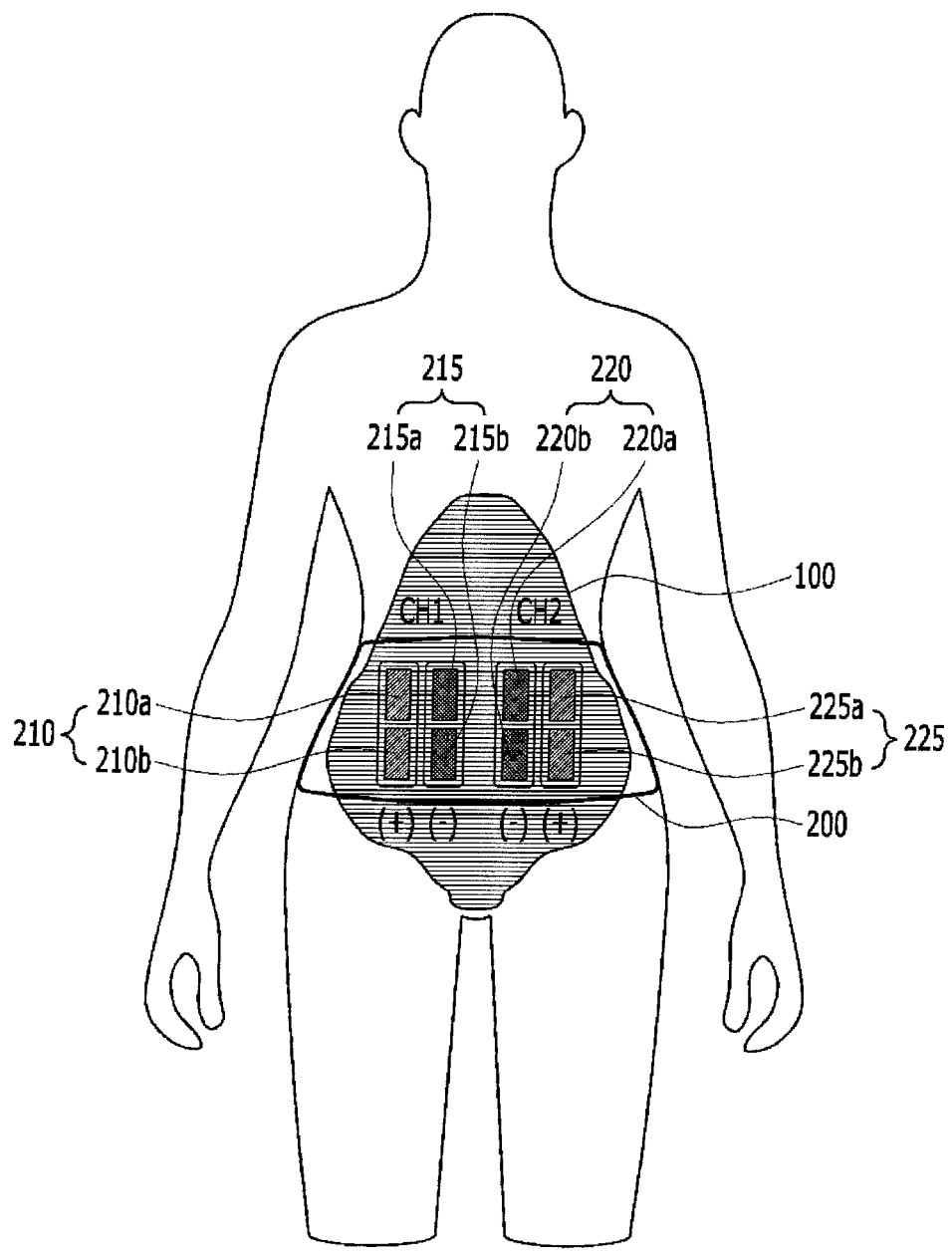
FIG. 2 is a diagram showing a front side of a person who wears a wearable instrument including electrode channels for strengthening core muscles of an abdominal region according to the present invention.
Figure 3:
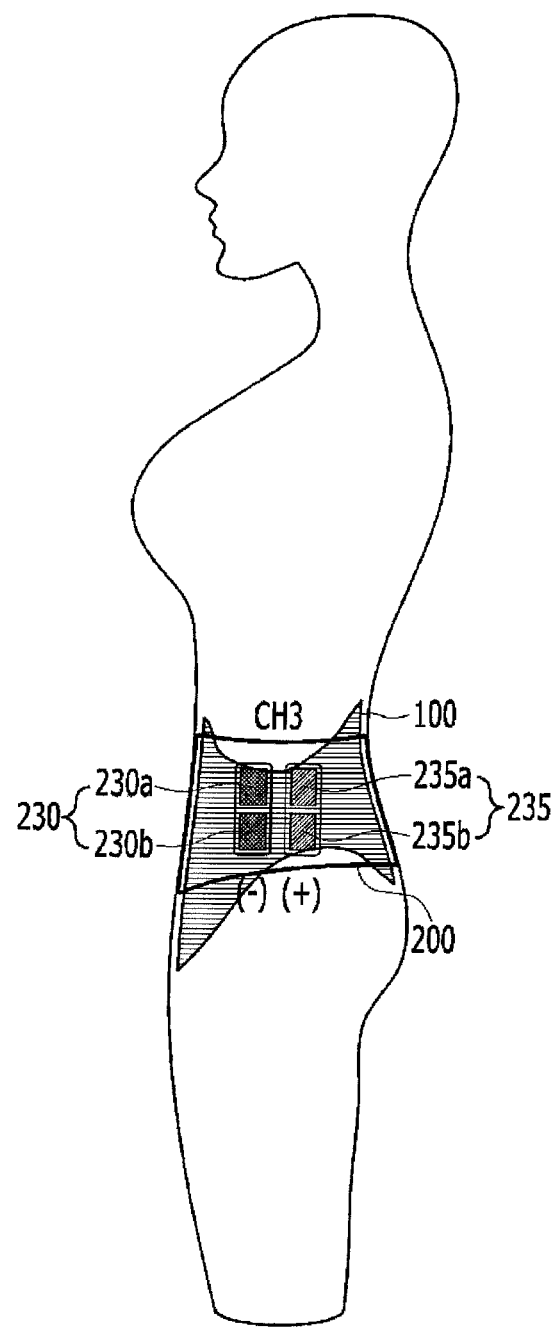
FIG. 3 is a diagram showing a left side of a person who wears a wearable instrument including electrostimulation pads for strengthening core muscles of an abdominal region according to the present invention.
Figure 4:
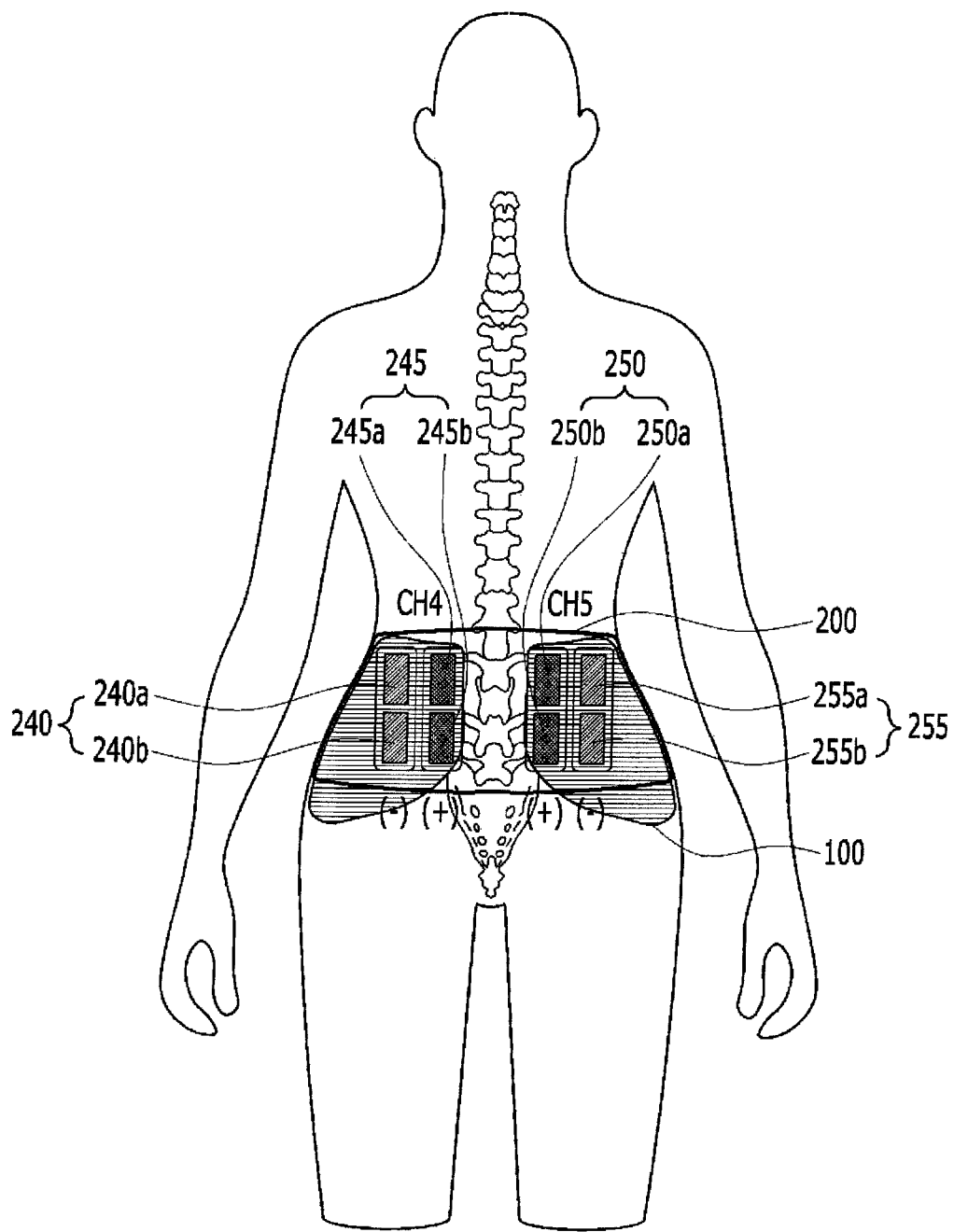
FIG. 4 is a diagram showing a rear side of a person who wears a wearable instrument including electrostimulation pads for strengthening core muscles of an abdominal region according to the present invention.
Figure 5:
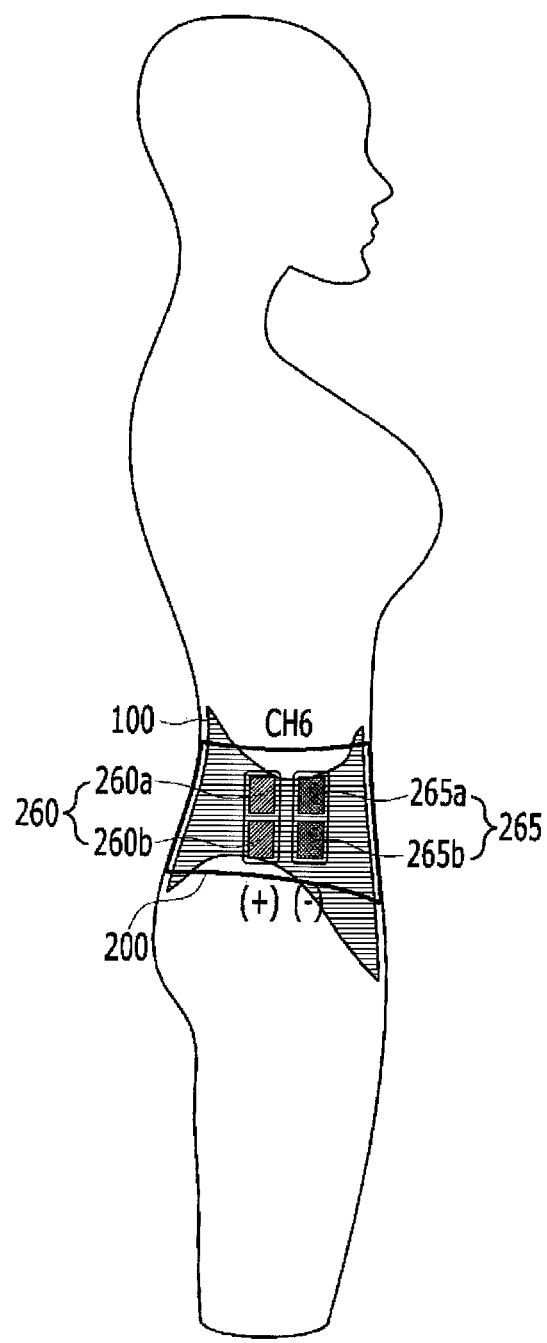
FIG. 5 is a diagram showing a right side of a person who wears a wearable instrument including electrostimulation pads strengthening core muscles of an abdominal region according to the present invention.

Arrangement of electrode channels associated with transversus abdominis of the human body will be described with reference to FIGS. 2 to 6. As described below, electrode channels are formed on a right abdominal region and a left abdominal region of a front side of the human body as shown in FIG. 2, both flanks of the human body as shown in FIGS. 3 and 5, and a left-lumbar region and a left-lumbar region of a rear side of the human body as shown in FIG. 4. The order of electrode channels is exemplary and may be changed.

FIG. 2 is a diagram showing a front side of a person who wears a wearable instrument including electrode channels for strengthening core muscles of an abdominal region according to the present invention.

The wearable instrument 200 including the electrode channels for strengthening the core muscles of the abdominal region according to the present invention is worn over a transversus abdominis 100 formed from the bottom of the diaphragm to the top of the pelvic floor muscle at the front side of the human body, as shown in FIG. 2. The wearable instrument 200 is worn over the abdominal region of a user and has a large width to cover most of the transversus abdominis 100. In addition, although the wearable instrument 200 has upper and lower ends relatively parallel to each other and has a rectangular shape in the shown example, the wearable instrument may have a diamond shape by extending the upper end of the center of the front side of the wearable instrument upward and extending the lower end downward according the shape of the transversus abdominis 100.

Referring to FIG. 2, a first electrode channel CH1 is formed on the right abdominal region of the front side of the human body and a second electrode channel CH2 is formed on the left abdominal region. The first electrode channel CH1 is configured such that a first positive-terminal strip 210 and a first negative-terminal strip 215 form an electrode pair. The second electrode channel CH2 is configured such that a second positive-terminal strip 220 and a second negative-terminal strip 225 form an electrode pair.

Hereinafter, the other electrode channels described below with reference to FIGS. 3 to 5 are configured such that a positive-terminal strip and a negative-terminal strip form an electrode pair. As the structure of the electrode pair, for example, the structure of the first electrode channel CH1 will be representatively described in detail.

In FIGS. 2 to 6, the transversus abdominis 100 is horizontally hatched. The transversus abdominis 100 is a horizontally striped muscle. In the present invention, the first positive-terminal strip 210 and the first negative-terminal strip 215 extend on the wearable instrument 200 in a vertical direction to cross the stripe direction of the transversus abdominis 100, thereby having a band shape. In addition, the first positive-terminal strip 210 and the first negative-terminal strip 215 are spaced apart from each other in a horizontal direction such that a pulse signal is delivered in the stripe direction of the transversus abdominis 100.

In the first positive-terminal strip 210, a plurality of first positive terminals 210a and 210b may be vertically-divisionally formed on a positive insulating film 212 insulated from the wearable instrument 200. Similarly, in the first negative-terminal strip 215, a plurality of first negative terminals 215a and 215b may be vertically-divisionally formed on a negative insulating film 217 insulated from the wearable instrument 200.

Figure 7:
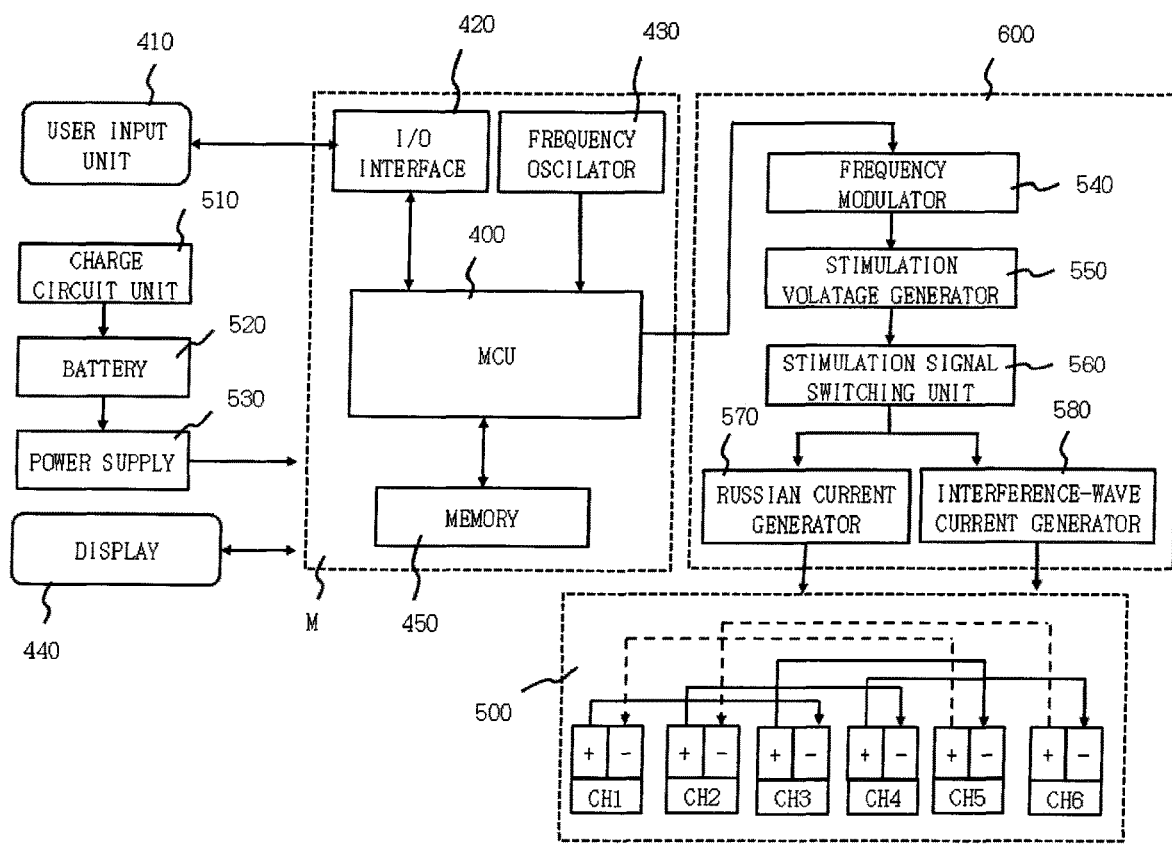
FIG. 7 is a schematic block diagram showing a drive device of electrode channels for strengthening core muscles of an abdominal region according to the present invention.

Although two first positive terminals 210a and 210b have the same area in the shown example, the areas of the first positive terminals 210a and 210b may be different from each other. In addition, in the first positive-terminal strip 210, as shown in FIG. 7, two of three first positive terminals 210a, 210b and 210c may have the same area and the remaining one first positive terminal may have a different area.

A frequency supply unit configured in the wearable instrument 200 applies a pulse signal having a predetermined frequency between the first positive-terminal strip 210 and the first negative-terminal strip 215. At this time, the pulse signal is applied to the first positive terminal 210a of the first positive-terminal strip 210 configuring the first electrode channel CH1 and the second negative terminal 225a of the second negative-terminal strip 225 configuring the second electrode channel CH2, and is applied to the second positive terminal 210b of the first positive-terminal strip 210 and the second negative terminal 225b of the second negative-terminal strip 225 of the second negative-terminal strip 225 configuring the second electrode channel CH2.

In addition, the pulse signal of the frequency supply unit configured in the wearable instrument 200 is applied to the first positive terminal 220a of the second positive-terminal strip 220 configuring the second electrode channel CH2 and the first negative terminal 215a of the first negative-terminal strip 215 configuring the first electrode channel CH1, and is applied to the second positive terminal 220b of the second positive-terminal strip 220 and the second negative terminal 215b of the first negative-terminal strip 215 configuring the first electrode channel CH1.

In the present invention, the pulse signal is applied to the first positive-terminal strip 210 of the first electrode channel CH1, the second negative-terminal strip 225 of the second electrode channel CH2 and the positive terminal and the negative terminal of the second positive-terminal strip 220 and the first negative-terminal strip 215 to permeate into internal organs and visceral fat.

Meanwhile, the pulse signal output from the frequency supply unit to the first electrode channel CH1 and the second electrode channel CH2 may be configured in a Russian current waveform, an interference-wave current waveform or a combinational waveform obtained by alternately applying Russian current and interference-wave current.

At this time, the frequency supply unit may apply the pulse signal to only the first positive terminal 210a and the first negative terminal 215a provided at the upper abdominal region, thereby operating in an upper abdominis training mode. Similarly, the frequency supply unit may apply the pulse signal to only the first positive terminal 210b and the first negative terminal 215b provided at the lower abdominal region, thereby operating in a lower abdominis training mode.

In addition, the frequency supply unit may apply the pulse signal over the first positive-terminal strip 210 and the first negative-terminal strip 215, thereby operating in the entire abdominis training mode for applying electrostimulation over the entire region of the transversus abdominis 100. That is, the electrostimulation device of the present invention provides an environment capable of selecting stimulation of the upper abdominal region, the lower abdominal region and the entire abdominal region.

Referring to FIG. 2, in the first electrode channel CH1, the first positive-terminal strip 210 is provided at the outer side of the right abdominal region and the first negative-terminal strip 215 is provided near the navel. When the frequency supply unit applies the pulse signal between the first positive-terminal strip 210 and the first negative-terminal strip 215, electrostimulation is applied from the outside of the right abdominal region toward the navel such that the transversus abdominis 100 is contracted inward. In an idle period in which electrostimulation is released, the muscle is relaxed in an opposite direction of the muscular contraction direction. Since the contraction and relaxation directions of the transversus abdominis 100 are similar to an actual contraction and relaxation direction by actual core-muscle contraction training, when core-muscle training and electrostimulation according to the present invention are combined, muscle strengthening effects can be further increased along with correction of posture.

In the example of FIG. 2, the plurality of second positive terminals 220a and 220b are vertically-divisionally formed in the second positive-terminal strip 220 configuring the second electrode channel CH2 and the plurality of second negative terminals 225a and 225b are vertically-divisionally formed in the second negative-terminal strip 225.

FIG. 3 is a diagram showing a left side of a person who wears a wearable instrument including electrostimulation pads for strengthening core muscles of an abdominal region according to the present invention, in which a third electrode channel CH3 is provided at the left flank of the human body. Referring to FIG. 3, a plurality of third positive terminals 230a and 230b is vertically-divisionally formed in a third positive-terminal strip 230 configuring the third electrode channel CH3 and a plurality of third negative terminals 235a and 235b is vertically-divisionally formed in a third negative-terminal strip 235.

FIG. 4 is a diagram showing a rear side of a person wearing a wearable instrument including electrostimulation pads for strengthening core muscles of an abdominal region according to the present invention, in which a fourth electrode channel CH4 is provided at a left-lumbar region of a rear side of the human body and a fifth channel CH5 is provided at a right-lumbar region of the rear side of the human body. Referring to FIG. 4, a plurality of fourth positive terminals 240a and 240b is vertically-divisionally formed in a fourth positive-terminal strip 240 configuring the fourth electrode channel CH4 and a plurality of fourth negative terminals 245a and 245b is vertically-divisionally formed in a fourth negative-terminal strip 245.

In addition, a plurality of fifth positive terminals 250a and 250b is vertically-divisionally formed in a fifth positive-terminal strip 250 configuring the fifth electrode channel CH5 and a plurality of negative terminals 255a and 255b is vertically-divisionally formed in the fifth negative-terminal strip 255.

FIG. 5 is a diagram showing a right side of a person who wears a wearable instrument including electrostimulation pads strengthening core muscles of an abdominal region according to the present invention, in which a sixth electrode channel CH6 is provided at a right flank of the human body. Referring to FIG. 5, a plurality of sixth positive terminals 260a and 260b is vertically-divisionally formed in a sixth positive-terminal strip 260 configuring the sixth electrode channel CH6 and a plurality of sixth negative terminals 265a and 265b is vertically-divisionally formed in a sixth negative-terminal strip 265.

The structure of each of the second electrode channel CH2 to the sixth electrode channel CH6 has an electrode pair of a positive-terminal strip and a negative-terminal strip, similarly to the structure of the first electrode channel CH1.

In addition, in the second electrode channel CH2, the second positive-terminal strip 220 is provided at the outside of the left abdominal region and the second negative-terminal strip 225 is provided near the navel. Similarly to the first electrode channel CH1, electrostimulation is applied from the outside of the left abdominal region toward the navel, thereby contracting the muscle. That is, the contraction and relaxation direction of the muscle is similar to the contraction and relaxation direction in actual abdominal muscle training.

Similarly, even in each of the third electrode channel CH3 to the sixth electrode channel CH6, the muscle is stimulated in the same muscle contraction and relaxation direction as when actually training the transversus abdominis 100, thereby further increasing muscle strengthening effects when abdominal muscle training and electrostimulation according to the present invention are combined.

Figure 6:
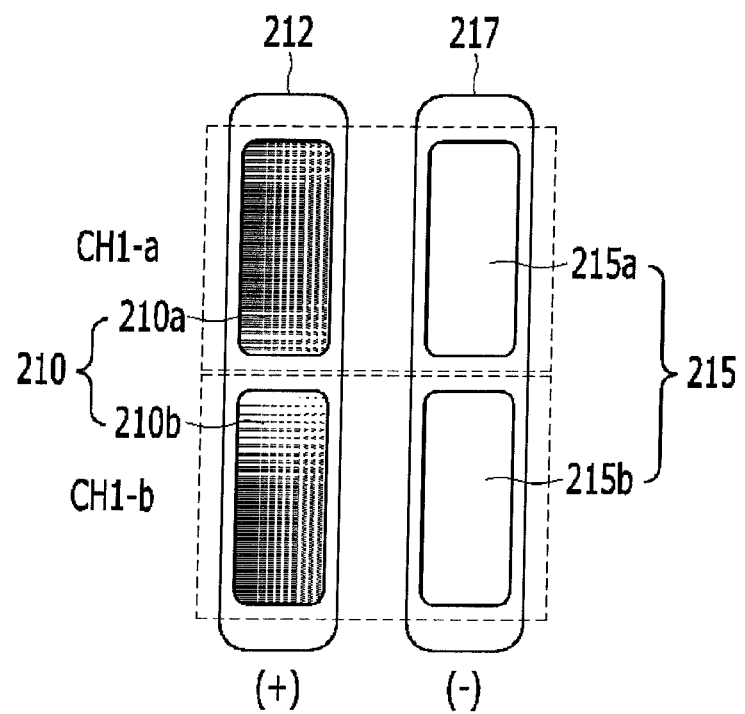
FIG. 6 is a diagram showing a first electrode channel in a wearable instrument including electrode channels for strengthening core muscles of an abdominal region according to the present invention in greater detail.

FIG. 6 is a diagram showing a first electrode channel in a wearable instrument including electrode channels for strengthening core muscles of an abdominal region according to the present invention in greater detail.

As shown in FIG. 6, two first positive terminals 210a and 210b having the same area are divisionally formed in the first positive-terminal strip 210, and are insulated by a positive insulating film 212 from the wearable instrument 200. Two first negative terminals 215a and 215b having the same area are divisionally formed in the first negative-terminal strip 215 and are insulated by a negative insulating film 217 from the wearable instrument 200. Although not shown, each of the second electrode channel to the sixth electrode channel has the same electrode pair structure.

FIG. 7 is a schematic block diagram showing a drive device of electrode channels for strengthening core muscles of an abdominal region according to the present invention.

The drive device of the electrode channels for strengthening the core muscle according to the present invention includes the wearable instrument 200 worn by a user over an abdominal region thereof, the plurality of electrode channels CH1 to CH6 500 provided on the wearable instrument 200 and having the electrode pair including the positive-terminal strip and the negative-terminal strip contacting the body of the user, and the frequency supply unit 600 for applying the pulse signal having the predetermined frequency between the positive-terminal strip and the negative-terminal strip, as shown in FIG. 7. In addition, in order to drive the frequency supply unit 600, a microprocessor unit (MCU) 400, a user input unit 410, an I/O interface 420, a frequency oscillator 430, a display 440, a memory 450, a charging circuit unit 510, a battery 520, a power supply 530, a stimulation voltage generator 540, a frequency modulator 550, a stimulation signal switching output unit 560, a Russian current wave generator 570 and an interference-wave current generator 580 are included.

Here, the I/O interface 420, the frequency oscillator 430, the MCU 400 and the memory 450 are included in a main board M. Under control of the main board M, the frequency supply unit 600 operates to output Russian current and interference-wave current, thereby driving the electrode channel 500.

The user input unit 410 includes an ON/OFF button for enabling the user to operate the drive device of the electro-stimulation pad of the present invention, a key input unit for selecting a stimulation mode, etc. At this time, in the case of a portable terminal or a smartphone, the user input unit 410 may include a touch panel built in the display 440 as the key input unit.

The I/O interface 420 is an input/output interface for receiving an operation command of the frequency supply unit as a wireless signal. For example, upon receiving an infrared signal from an infrared type remote controller, the microprocessor unit 400 may output an operation command of the frequency supply unit in correspondence with an input signal.

The I/O interface 420 is not limited to the infrared signal interface and may be replaced with another short-range wireless communication type interface or may be configured by combining various wireless-signal input type interfaces.

The communication unit (not shown) may include a short-range wireless communication module, a mobile communication module, a wireless Internet module, etc. The short-range wireless communication module performs communication with a smartphone or another communication device over a short-range wireless network and may include Bluetooth, Wi-Fi, ZigBee, etc.

For example, the microprocessor unit 400 may perform short-range wireless communication with the smartphone, communicate with an application (App) installed in the smartphone to provide an operation state of the frequency supply unit on a screen, or receive an input signal through the application of the smartphone to control the frequency supply unit.

The mobile communication module may transmit and receive a voice call signal, wireless data, a multimedia message, etc. through a remote management server or a mobile communication terminal and a mobile communication network and may include a CDMA (Code Division Multiple Access) module or an LTE (Long Term Evolution) module. The wireless Internet module may include wireless Internet access modules such as WLAN (Wireless LAN), WiBro (Wireless Broadband), WiMax (World Interoperability for Microwave Access) and HSDPA (High Speed Downlink Packet Access).

The microprocessor unit 400 may transmit operation state information of the frequency supply unit to the remote management server using the mobile communication module and the wireless Internet module. The management server may monitor the usage and form of the electrostimulation device of the user through received information, manage a database per user to output a stimulation training command or collect data on usage results of a plurality of users to refer to the data for upgrade of the electrostimulation device and development of future products.

The display 440 may display the operation state of the frequency supply unit and include an LCD (Liquid Crystal Display), an organic light emitting diode, an AMOLED (Active Matrix Organic Light Emitting Diode), a flexible display, etc. The display 440 may output a graphical user interface (GUI) related to the electrostimulation device according to the present invention on a screen thereof and display a stimulated region along with the image of the human body.

In addition, the display 440 may display the contraction and relaxation state of the abdominal muscle in the form of animation. A touch panel for receiving user touch input and generating an input signal may be included in the display 440.

The memory 450 may store a control program of the frequency supply unit, an operation history of the electrostimulation device, user information, etc. and include at least one of a flash memory, a hard disk, a multimedia card micro type, a card type memory (e.g., an SD or XD memory, etc.), a Random Access Memory (RAM), an SRAM (Static Random Access Memory), a Read Only Memory (ROM), an EEPROM (Electrically Erasable Programmable Read Only Memory), a PROM (Programmable Read Only Memory), a magnetic memory, a magnetic disk and an optical disc.

Meanwhile, the drive device according to the present invention may include a commercial AC power source, a battery or selectively use the commercial AC power source and the battery. The power supply 530 may be an AC-to-DC converter for applying commercial AC power to the internal components of the device and converting the commercial AC power into constant-current DC power for generating a stimulation voltage. Alternatively, the power supply 530 may be configured to boost or drop the output of the battery 520 as the DC-to-DC converter.

The frequency supply unit 600 may include the microprocessor unit 400 for controlling operation of each component, a stimulation voltage generator 540, a frequency modulator 550, a stimulation signal switching output unit 560, a Russian current generator 570 and an interference-wave current generator 580.

The stimulation voltage generator 540 generates a voltage for electrostimulation from the output of the power supply 530. The frequency modulator 550 modulates the output of the stimulation voltage generator 540 into a signal having a predetermined frequency and operates upon receiving a frequency from the oscillator 430 for generating an oscillation frequency.

By switching operation of the stimulation signal switching output unit 560, Russian current or interference-wave current may be delivered between the positive-terminal strip and the negative-terminal strip of each electrode channel or no current is delivered as an idle mode.

The Russian current generator 570 generates current having a middle frequency of 2,000 Hz to 5,000 Hz from the output from the frequency modulator 550. Current having the middle frequency is a sine signal and is suitable for stimulating the transversus abdominis 100 located at the innermost side of the abdominal muscle. Preferably, Russian current has a frequency band of 2,000 to 3,000 Hz.

The interference-wave current generator 580 generates and crosses different middle frequencies in a middle frequency band of 2,000 to 5,000 Hz from the output of the frequency modulator 550, thereby generating interference-wave current. For example, when a frequency of 2,800 Hz is applied to the first electrode channel CH1 and a frequency of 2,850 Hz is applied to the second electrode channel CH2, the two frequencies are crossed with each other, thereby generating an interference-wave current of 50 Hz.

Since such an interference-wave current having a higher frequency band is used, muscle pain and muscle fatigue caused by use of Russian current are relieved. The interference-wave current permeates into cellulite of fat to increase effects of breaking down fat.

For example, the microprocessor unit 400 performs control to alternately apply Russian current and interference-wave current in one period of the pulse signal applied to each of the electrode channels CH1 to CH6. If strengthening of the transversus abdominis 100 is focused upon, a frequency ratio of Russian current to interference-wave current may be controlled to 1:2.

If a user first uses the electrostimulation device according to the present invention or desires weak stimulation, the frequency ratio of Russian current to interference-wave current may be controlled to 1:5.

Under control of the microprocessor unit 400 and the stimulation signal switching output unit 560, the output of the Russian current generator 570 and the output of the interference-wave current generator 580 are switched and applied to the electrode channel. By switching operation of the stimulation signal switching output unit 560, Russian current or interference-wave current may be delivered between the positive-terminal strip and the negative-terminal strip of each of the electrode channels CH1 to CH6 or no current is delivered as an idle mode.

In the present invention, the current of the Russian current generator 570 and the interference-wave current of the interference-wave current generator 580 are applied to each of the electrode channels CH1 to CH6 according to switching operation of the stimulation signal switching output unit 560. At this time, Russian current and interference-wave current are not applied from the positive terminal to the positive terminal of each of the electrode channels CH1 to CH6 but are applied to each of the electrode channels CH1 to CH6 disposed in a diagonal line or in a crossing direction.

That is, control is performed through the MCU 400 such that Russian current and interference-wave current are selectively applied from the positive terminal of the first electrode channel CH1 to the negative terminal of the third electrode channel CH3, from the positive terminal of the second electrode channel CH2 to the negative terminal of the fourth electrode channel CH4, from the positive terminal of the third electrode channel CH3 to the negative terminal of the fifth electrode channel CH5, from the positive terminal of the fourth electrode channel CH4 to the negative terminal of the sixth electrode channel CH6, from the positive terminal of the fifth electrode channel CH5 to the negative terminal of the first electrode channel CH1, and from the positive terminal of the sixth electrode channel CH6 to the negative terminal of the second electrode channel CH2.

Meanwhile, when Russian current or interference-wave current is applied from the positive terminal to the negative terminal of each of the electrode channels CH1 to CH6, Russian current or interference-wave current is not applied to the positive terminal and the negative terminal of each electrode channel but is applied from the positive terminal to the negative terminal of a neighboring electrode channel thereof.

In the embodiment of the present invention, the Russian current generator 570 may apply Russian current from the positive-terminal strip to the negative-terminal strip of each electrode channel 500.

The interference-wave current generator 580 applies different interference-wave currents, that is, interference-wave upper-layer current and interference-wave lower-layer current, to the upper-layer electrode channels and the lower-layer electrode channels to generate interference between two electrode channels, in a state of dividing the electrode channels 500 divisionally provided at a predetermined interval into the upper-layer electrode channels and the lower-layer electrode channels to generate interference between interference-wave currents.

Figure 8:
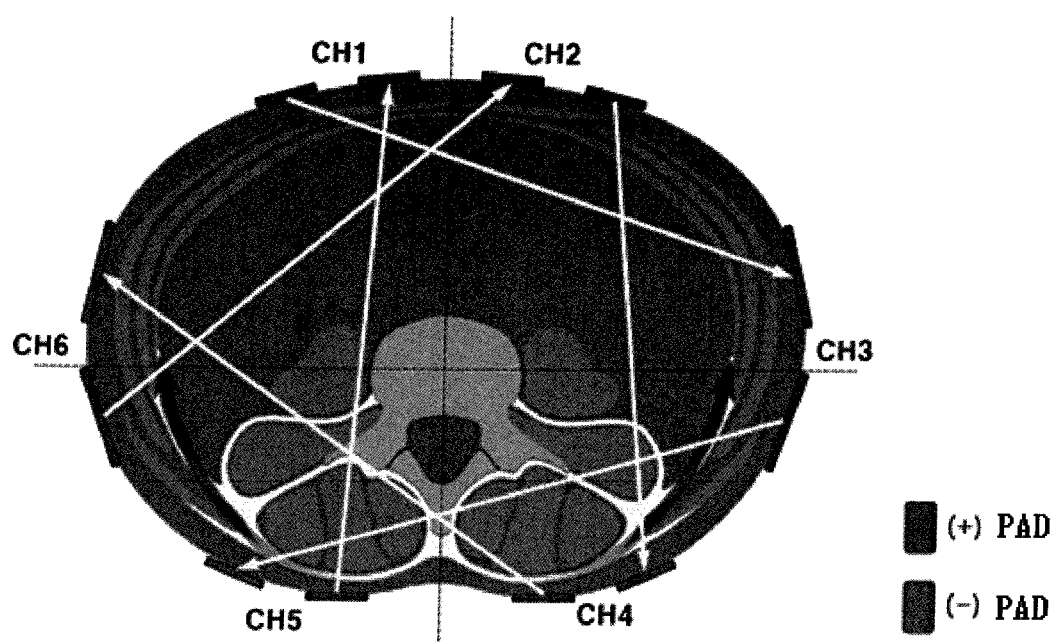
FIG. 8 is a diagram showing an example of applying interference-wave upper-layer current to electrode channels provided on an abdominal region in FIG. 7.

FIG. 8 is a diagram showing an example of applying interference-wave upper-layer current to electrode channels provided on an abdominal region in FIG. 7.

As shown in FIG. 8, interference-wave upper-layer current is applied from the positive-terminal strip of the first electrode channel CH1 to the negative-terminal strip of the third electrode channel CH3 among the first to sixth electrode channels CH1 to CH6 attached to the abdominal region of the user and interference-wave current is applied from the positive-terminal strip of the second electrode channel CH2 to the negative-terminal strip of the fourth electrode channel CH4.

In addition, interference-wave current is applied from the positive-terminal strip of the third electrode channel CH3 to the negative-terminal strip of the fifth electrode channel CH5, interference-wave current is applied from the positive-terminal strip of the fourth electrode channel CH4 to the negative-terminal strip of the sixth electrode channel CH6, and interference-wave current is applied from the positive-terminal strip of the fifth electrode channel CH5 to the negative-terminal strip of the first electrode channel CH1.

In addition, interference-wave current is selectively applied from the positive-terminal strip of the sixth electrode channel CH6 to the negative-terminal strip of the second electrode channel CH2.

At this time, interference-wave upper-layer current applied from the positive-terminal strip to the negative-terminal strip of each of the first to sixth electrode channels CH1 to CH6 has a frequency of 2,800 Hz.

Figure 9:
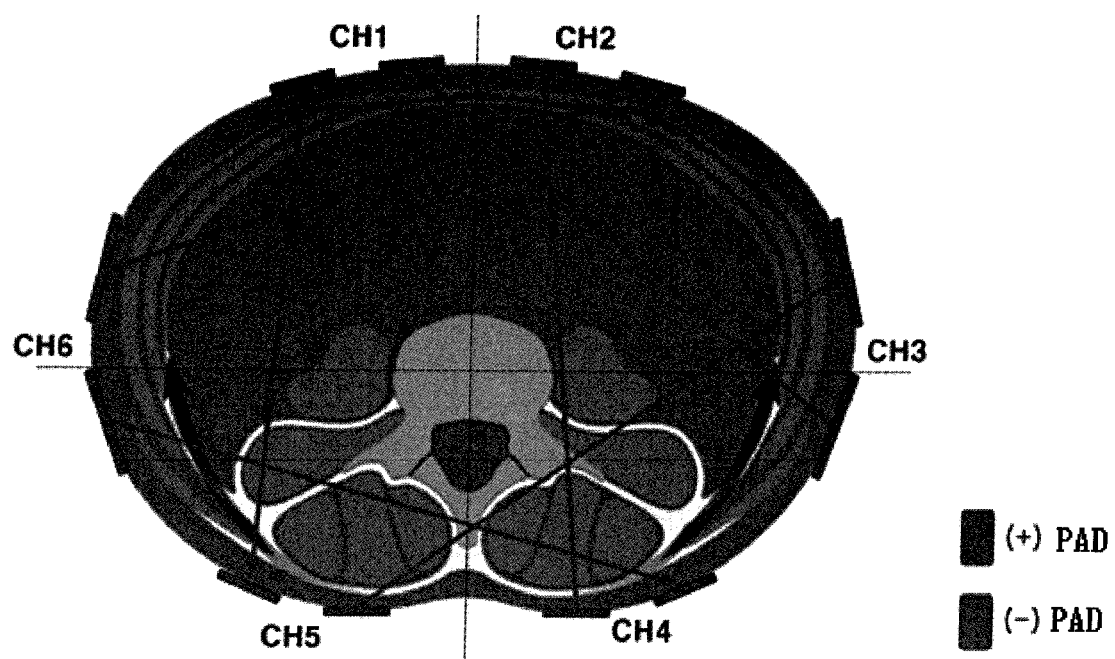
FIG. 9 is a diagram showing an example of applying interference-wave lower-layer current to electrode channels provided on an abdominal region in FIG. 7.

FIG. 9 is a diagram showing an example of applying interference-wave lower-layer current to electrode channels provided on an abdominal region in FIG. 7

As shown in FIG. 9, interference-wave lower-layer current is applied from the positive-terminal strip of the first electrode channel CH1 to the negative-terminal strip of the fifth electrode channel CH5 among the first to sixth electrode channels CH1 to CH6 attached to the abdominal region of the user, and interference-wave current is applied from the positive-terminal strip of the second electrode channel CH2 to the negative-terminal strip of the sixth electrode channel CH6.

In addition, interference-wave current is applied from the positive-terminal strip of the third electrode channel CH3 to the negative-terminal strip of the first electrode channel CH1, interference-wave current is applied from the positive-terminal strip of the fourth electrode channel CH4 to the negative-terminal strip of the second electrode channel CH2, and interference-wave current is applied from the positive-terminal strip of the fifth electrode channel CH5 to the negative-terminal strip of the third electrode channel CH3.

In addition, interference-wave lower-layer current is selectively applied from the positive-terminal strip of the sixth electrode channel CH6 to the negative-terminal strip of the fourth electrode channel CH4.

At this time, interference-wave lower-layer current applied from the negative-terminal strip to the negative-terminal strip of each of the first to sixth electrode channels CH1 to CH6 has a frequency of 2,850 Hz.

Figure 10:
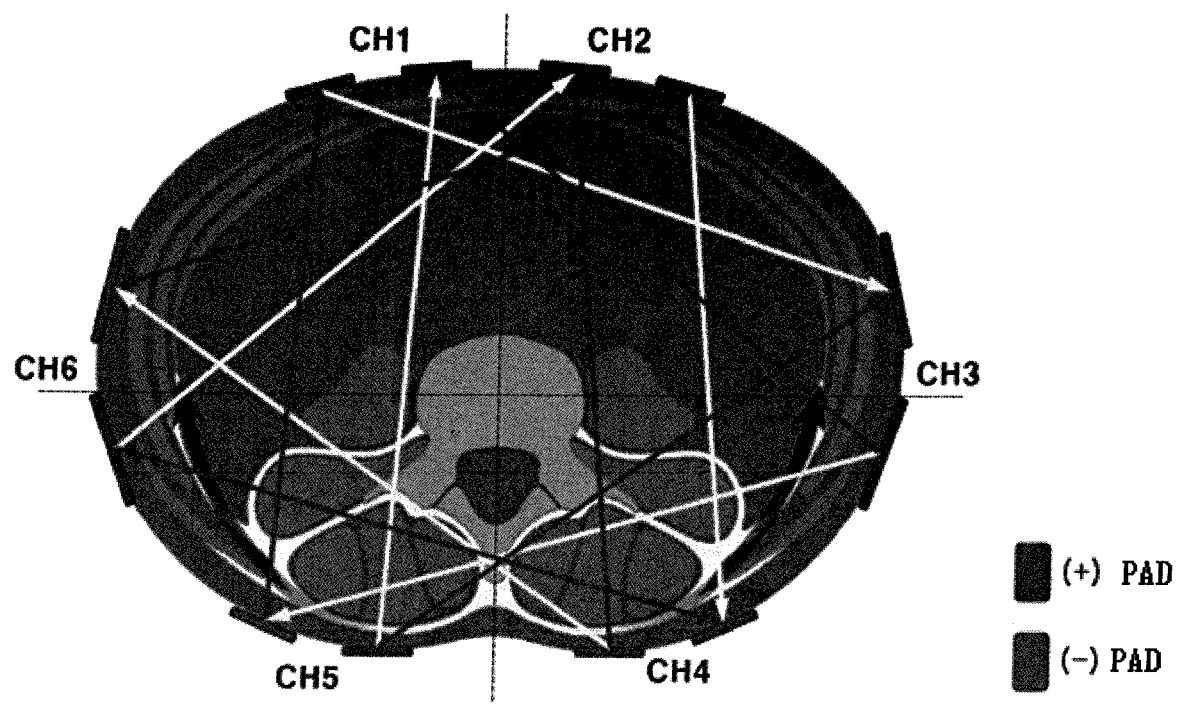
FIG. 10 is a diagram showing an example of applying interference-wave current to electrode channels provided on an abdominal region in FIG. 7.

FIG. 10 is a diagram showing an example of applying interference-wave current to electrode channels provided on an abdominal region in FIG. 7.

As shown in FIG. 10, interference-wave current is applied from the positive-terminal strip of the first electrode channel CH1 to the negative-terminal strips of the third electrode channel CH3 and the fifth electrode channel CH5 of the first to sixth electrode channels CH1 to CH6 attached to the abdominal region of the user, and interference-wave current is applied from the positive-terminal strip of the second electrode channel CH2 to the negative-terminal strips of the fourth electrode channel CH4 and the sixth electrode channel CH6.

In addition, interference-wave current is applied from the positive-terminal strip of the third electrode channel CH3 to the negative-terminal strips of the first electrode channel CH1 and the third electrode channel CH3, interference-wave current is applied from the positive-terminal strip of the fourth electrode channel CH4 to the negative-terminal strips of the second electrode channel CH2 and the sixth electrode channel CH6, and interference-wave current is applied from the positive-terminal strip of the fifth electrode channel CH5 to the negative-terminal strips of the first electrode channel CH1 and the third electrode channel CH3.

In addition, interference-wave lower-layer current is selectively applied from the positive-terminal strip of the sixth electrode channel CH6 to the negative-terminal strips of the second electrode channel CH2 and the fourth electrode channel CH4.

At this time, interference-wave current applied from the positive-terminal strip of each of the first to sixth electrode channels CH1 to CH6 to the negative-terminal strips of two separated electrode channels has a frequency of 2,800 Hz in the case of higher-layer current (yellow) and has a frequency of 2,850 Hz in the case of lower-layer current (violet).

Figure 11:
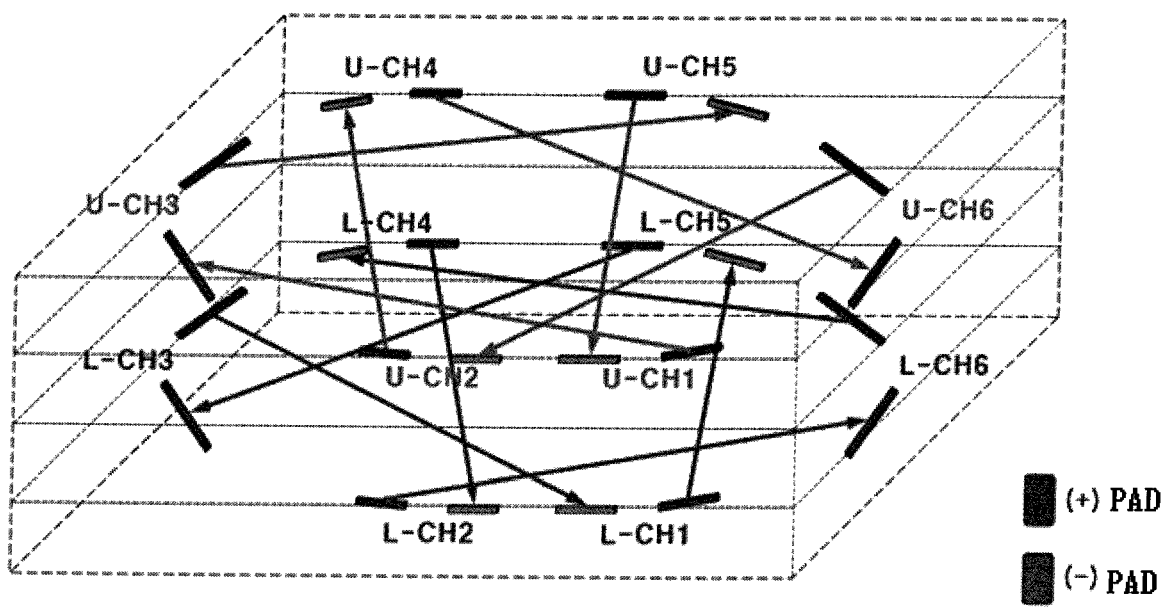
FIG. 11 is a diagram showing an example of applying interference-wave current to an upper-layer electrode channel and a lower-layer electrode channel, which are separated from each other, of the electrode channels of FIG. 10.

FIG. 11 is a diagram showing an example of applying interference-wave current to an upper-layer electrode channel and a lower-layer electrode channel, which are separated from each other, in the electrode channels of FIG. 10.

In FIG. 11, the same method as the method of applying interference-wave current to the positive-terminal strip and the negative-terminal strip of each electrode channel of FIG. 10 is used.

At this time, the upper-layer electrode channel is divided into U-CH1 to U-CH6 and the lower-layer electrode channel is divided into L-CH1 to L-CH6. Meanwhile, upper-layer current applied from the positive-terminal strip to the negative-terminal strip of the upper-layer electrode channel has a frequency of 2,800 Hz and is represented by green and lower-layer current applied from the positive-terminal strip to the negative-terminal strip of the lower-layer electrode channel has a frequency of 2,850 Hz and is represented by violet.

Figure 12:
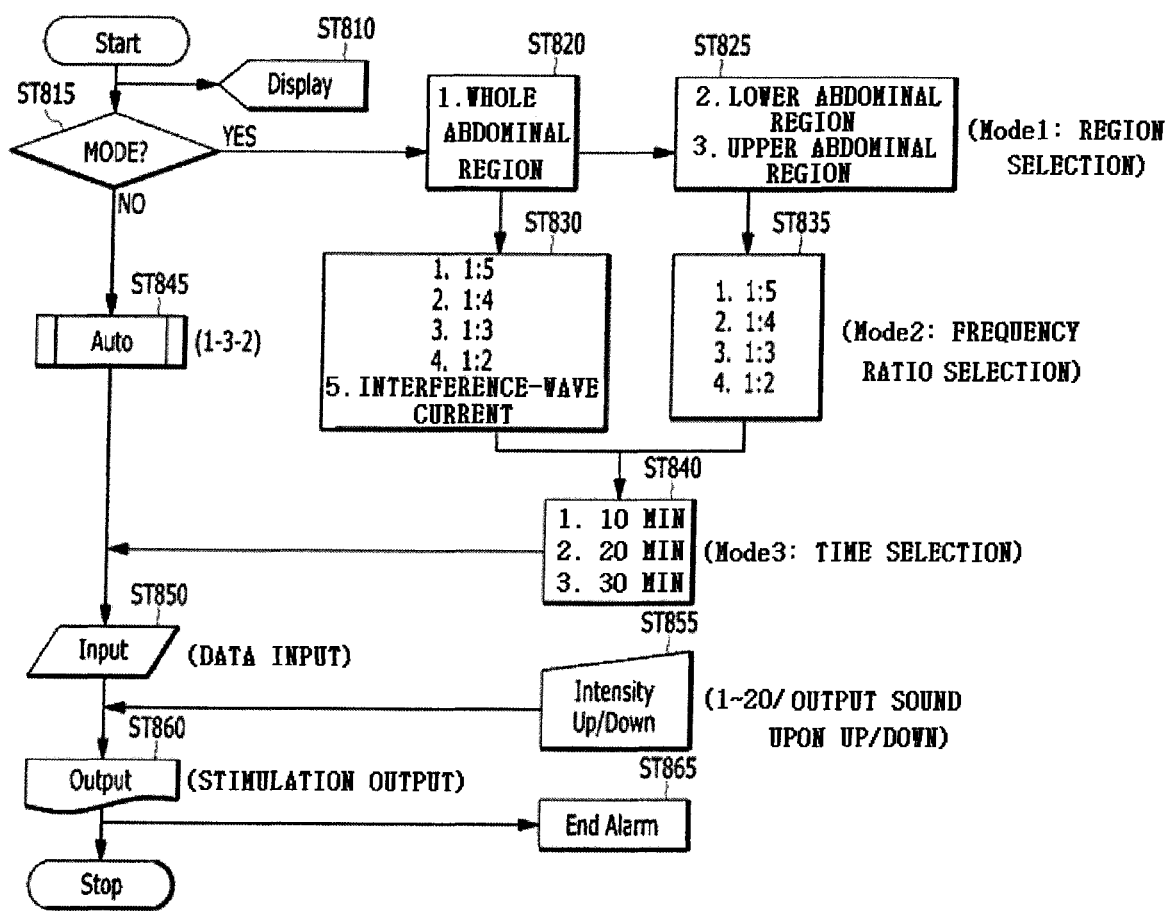
FIG. 12 is a flowchart illustrating operation states of the present invention.

FIG. 12 is a flowchart illustrating operation states of the present invention.

As shown in FIG. 12, when power is turned on in a state in which a user wears the wearable instrument 200 over an abdominal region, operation starts while a user interface screen is displayed on the display 440 (ST810). Booting of the device is finished, a mode selection screen is displayed on the display 440, and an auto mode or a manual mode is selected according to user input (ST815).

Subsequently, upon entering the manual mode, a region selection mode for selecting a stimulation region of an abdominal region is activated. At this time, an upper or lower abdominal region may be selected (ST820) and any one of the upper abdominal region and the lower abdominal region may be selected (ST825).

Subsequently, if the upper/lower abdominal stimulation mode is selected, a mode for selecting the frequency ratio of Russian current to interference-wave current is performed (ST830). The user may select one of the frequency ratios of 1:5, 1:4, 1:3 and 1:2 and the interference-wave current (mode in which only the interference-wave electrode is used without using Russian current) in this mode.

Even when one of the lower abdominal region and the upper abdominal region is selected, a mode for selecting the frequency ratio of Russian current to interference-wave current is performed (ST835).

Subsequently, if the mode for selecting the frequency ratio is finished, a mode for setting a stimulation time is performed (ST840). In this step, a stimulation time of 10 minutes, 20 minutes or 30 minutes may be selected.

If the auto mode is selected in step ST815 of selecting the mode, the auto mode is performed and the whole abdominal region, a frequency ratio of 1:3 and a stimulation time of 20 minutes are automatically selected (ST845). Of course, the items selected by the auto mode may be arbitrarily changed by the user.

Subsequently, when mode selection is finished, data on the modes input in the manual mode or modes selected in the auto mode is received (ST850). At this time, the user may adjust a stimulation intensity (ST855) and the stimulation intensity may be selectively adjusted while electrostimulation is applied to the upper/lower abdominal region.

For example, the microprocessor unit 400 may adjust the stimulation intensity by increasing or decreasing the maximum amplitude of Russian current or interference-wave current.

When data input is finished, the microprocessor unit 400 may output a control signal to operate the stimulation signal switching output unit 560 according to the input data (ST860). Whether Russian current or interference-wave current is applied is selected according to selection of the stimulation signal switching output unit 560.

Electrostimulation is applied to the upper/lower abdominal region according to the set mode. When a predetermined time has passed, an end alarm is output (ST865), and operation of the device ends.

Figure 13:
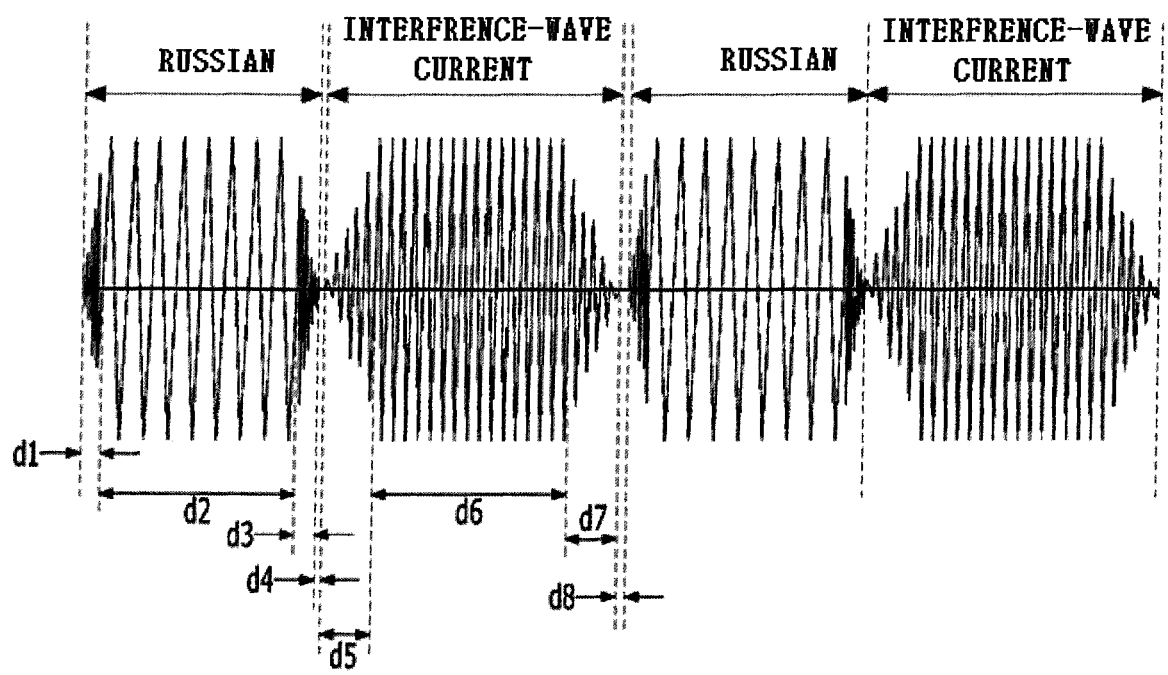
FIG. 13 is a waveform diagram showing electrostimulation waves according to the present invention.

FIG. 13 is a waveform diagram showing electrostimulation waves according to the present invention. FIG. 13 shows a state in which a stimulation wave is delivered to the whole abdominal region with a frequency ratio of 1:3 in a wave motion mode. The maximum amplitudes of Russian current and interference-wave current are actually different from each other but are shown as being equal to each other for understanding of the invention.

As shown in FIG. 13, the microprocessor unit 400 controls the stimulation signal switching output unit 560 such that Russian current and interference-wave current are alternately applied. Russian current is a signal for applying strong stimulation to the transversus abdominis 100, and the interference-wave current may be provided to relieve muscle pain and to relax to the user in the OFF period of Russian current.

Preferably, an idle period in which no signal is delivered is present between the Russian current and the interference-wave current. For example, an idle period having frequency output of 0 is about 1 second.

The output of one period has sections having different waveforms of d1 to d8. Each section with a frequency ratio of 1:3 will now be described.

First, d1 is a soft rising duration in which the amplitude of the wave gradually increases at the ON time of Russian current. When Russian current is suddenly applied, the muscles may be suddenly contracted and a sensitive user may experience discomfort. Therefore, in order to prevent this, the soft rising duration is set to apply Russian current. In this example, d1 has a length of about 2 seconds.

d2 is a duration in which Russian current having a maximum value is applied and has a length of 10 seconds. d3 is a soft falling duration in which the amplitude of the wave gradually decreases at the OFF time of Russian current. When strong electrostimulation suddenly disappears, the muscles may be suddenly relaxed, thereby reducing muscle strengthening effects. Therefore, the soft falling duration is set to gradually decrease Russian current. In this example, d3 has a length of 2 seconds.

d4 is an idle duration after Russian current is turned off and has a length of about 1 second. d5 is a soft rising duration in which the amplitude of the wave gradually increases at the ON time of the interference-wave current and has a length of 5 seconds.

d6 is a duration in which the interference-wave current having a maximum value is applied and has a length of 20 seconds, and d7 is a soft falling duration in which the amplitude of the wave gradually decreases at the OFF time of the interference-wave current and has a length of 5 seconds.

d8 is an idle duration after the interference-wave current is turned off and has a length of about 1 second.

Referring to the waveform diagram of FIG. 13, a time when Russian current having a maximum value is applied to substantially apply electrostimulation to the abdominal muscle is 10 seconds, the interference-wave current is a signal having 50 Hz or less, and electrostimulation is applied for 30 seconds, including the soft rising duration and the soft falling duration.

Meanwhile, the frequency ratio of 1:3 is set in order to uniformly apply electrostimulation to the whole region of the transversus abdominis 100, to relieve pain caused by electrostimulation and to maintain the sense of stability of the user. Since muscular strength and pain differ between users, the frequency ratio of the auto mode may be variously changed according to user settings.

The drive device of the electrode channel for strengthening the core muscles of the abdominal region according to the present invention has the following effects.

That is, it is possible to stimulate internal organs and visceral fat to improve circulation of body fluid in a body cavity of the abdominal region and to activate muscle membrane tissues while strengthening core muscles and increasing effects of removing abdominal fat by applying Russian current or interference-wave current from positive-terminal strips to negative-terminal strips of different electrode channels in the positive-terminal strips and the negative-terminal strips configuring a plurality of electrode channels.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A drive device of electrode channels for strengthening core muscles of an abdominal region, the drive device comprising;
   a wearable instrument worn by a user over an abdominal region;
   a plurality of electrode channels formed by an electrode pair of a positive-terminal strip and a negative-terminal strip provided on the wearable instrument and contacting a body of the user; and
   a frequency supply unit, including:
   a stimulation voltage generator configured to generate a voltage for electrostimulation:
   a frequency modulator configured to modulate output of the stimulation voltage generator into a signal having a predetermined frequency:
   a Russian current generator configured to generate current having a middle frequency of 2.000 Hz to 5.000 Hz from the output of the frequency modulator:
   an interference-wave current generator configured to generate and cross different middle frequencies from output of the frequency modulator to generate an interference-wave current:
   a stimulation signal switching unit configured to switch and apply output of the Russian current generator and output of the interference-wave current generator to the electrode channels: and
   a microprocessor unit configured to control the Russian current and the interference-wave current are alternately applied to the positive-terminal strip of one of the plurality of electrode channels and the negative-terminal strip of another electrode channel.

2. The drive device according to claim 1, wherein the electrode channels are formed on front right and left abdominal regions, both flanks, and rear left-lumbar and right-lumbar regions of the body of the user.

3. The drive device according to claim 1, wherein the plurality of electrode channels is divided into upper-layer electrode channels and lower-layer electrode channels and different interference-wave currents are applied to the positive-terminal strips and the negative-wave strips of the upper-layer electrode channels and the lower-layer electrode channels.

4. The drive device according to claim 3, wherein interference-wave current of 2,800 Hz is applied to the upper-layer electrode channels and interference-wave current of 2,850 Hz is applied to the lower-layer electrode channels.

5. The drive device according to claim 1, wherein the microprocessor unit performs control to alternately apply the Russian current and the interference-wave current in one period of a pulse signal applied to the electrode channels.

6. The drive device according to claim 1, wherein the positive-terminal strip and the negative-terminal strip have a band shape extending from the wearable instrument in a vertical direction to cross a stripe direction of a transversus abdominis of the body, and the positive-terminal strip and the negative-terminal strip are spaced apart from each other in a horizontal direction, such that Russian current or interference-wave current is delivered in the stripe direction of the transversus abdominis.

7. The drive device according to claim 1, wherein a plurality of positive terminals is vertically-divisionally formed on a positive insulating film insulated from the wearable instrument in the positive-terminal strip, and a plurality of negative terminals is vertically-divisionally formed on a negative insulating film insulated from the wearable instrument in the negative-terminal strip.

8. A drive device of electrode channels for strengthening core muscles of an abdominal region, the drive device comprising:
   a wearable instrument worn by a user over an abdominal region;
   a plurality of electrode channels formed by an electrode pair of a positive-terminal strip and a negative-terminal strip provided on the wearable instrument at a constant interval and contacting a body of the user; and
   a frequency supply unit including:
   a stimulation voltage generator configured to generate a voltage for electrostimulation; a frequency modulator for modulating output of the stimulation voltage generator into a signal having a predetermined frequency;
   a Russian current generator configured to generate current having a middle frequency of 2.000 Hz to 5.000 Hz from the output of the frequency modulator;
   an interference-wave current generator configured to generate and cross different middle frequencies from output of the frequency modulator to generate interference-wave current;
   a stimulation signal switching unit configured to switch and apply output of the Russian current generator and output of the interference-wave current generator to the electrode channels; and
   a microprocessor unit configured to repeatedly perform sections in order including:
   a duration in which the amplitude of the middle frequency current gradually increases by operating the Russian current generator (d1);
   a duration in which the amplitude of the middle frequency current has a maximum value (d2);
   a duration in which the amplitude of the middle frequency current gradually decreases (d3);
   a duration in which the amplitude of the middle frequency current has 0 value (d4);
   a duration in which the amplitude of the interference-wave current gradually increases by operating the interference-wave current generator after Russian current generator is turned off (d5);
   a duration in which the amplitude of the interference-wave current has a maximum value (d6);
   a duration in which the amplitude of the interference-wave current gradually decreases (d7); and
   a duration in which the amplitude of the interference-wave current has 0 value (d8).

9. A drive device of electrode channels for strengthening core muscles of an abdominal region, the drive device comprising:
   a wearable instrument worn by a user over an abdominal region;
   first to sixth electrode channels formed by an electrode pair of a positive-terminal strip and a negative-terminal strip provided on the wearable instrument at a constant interval and contacting a body of the user; and
   a frequency supply unit configured to generate and alternately applying Russian current having a middle frequency and interference-wave current between the positive-terminal strips and the negative-terminal strips of the first to sixth electrode channels, the frequency supply unit including:
   a stimulation voltage generator configured to generate a voltage for electrostimulation; a frequency modulator for modulating output of the stimulation voltage generator into a signal having a predetermined frequency;

a Russian current generator configured to generate current having the middle frequency of 2,000 Hz to 5.000 Hz from the output of the frequency modulator;

an interference-wave current generator configured to generate and cross different middle frequencies from output of the frequency modulator to generate interference-wave current;

a stimulation signal switching unit configured to switch and apply output of the Russian current generator and output of the interference-wave current generator to the electrode channels; and a microprocessor unit configured to control the Russian current and Interference-wave current are alternately applied to the positive-terminal strip of one of the first to sixth electrode channels and the negative-terminal strip of another electrode channel, wherein the frequency supply unit configured in the wearable instrument is configured to:

apply interference-wave current from a positive-terminal strip of the first electrode channel to negative-terminal strips of the third electrode channel and the fifth electrode channel, apply interference-wave current from a positive-terminal strip of the second electrode channel to negative-terminal strips of the fourth electrode channel and the sixth electrode channel, apply interference-wave current from a positive-terminal strip of the third electrode channel to negative-terminal strips of the first electrode channel and the third electrode channel, applies interference-wave current from a positive-terminal strip of the fourth electrode channel to negative-terminal strips of the second electrode channel and the sixth electrode channel, apply interference-wave current from a positive-terminal strip of the fifth electrode channel to negative-terminal strips of the first electrode channel and the third electrode channel, and apply interference-wave lower-layer current from a positive-terminal strip of the sixth electrode channel to negative-terminal strips of the second electrode channel and the fourth electrode channel.

* * * * *